United States Patent [19]
Tucker

[11] Patent Number: 6,045,359
[45] Date of Patent: *Apr. 4, 2000

[54] DENTAL IMPRESSION TRAY

[76] Inventor: John Hilliard Tucker, 809 W. 26th St., Erie, Pa. 16508

[*] Notice: This patent is subject to a terminal disclaimer.

[21] Appl. No.: 09/197,796

[22] Filed: Nov. 23, 1998

Related U.S. Application Data

[63] Continuation of application No. 08/900,618, Jul. 25, 1997, Pat. No. 5,890,895.

[51] Int. Cl.[7] .................................................... A61C 9/00
[52] U.S. Cl. ................................................................ 433/37
[58] Field of Search ................................ 433/34–38, 41, 433/42, 45, 47, 214

[56] References Cited

U.S. PATENT DOCUMENTS

| | | |
|---|---|---|
| 1,861,645 | 6/1932 | Stein . |
| 2,426,388 | 8/1947 | Chartrand . |
| 2,529,429 | 11/1950 | Spiro . |
| 2,634,500 | 4/1953 | McAdoo . |
| 2,758,374 | 8/1956 | Fisher et al. . |
| 3,207,153 | 9/1965 | Goldstein ................................ 128/136 |
| 3,736,663 | 6/1973 | White . |
| 3,978,585 | 9/1976 | Holcomb . |
| 4,003,132 | 1/1977 | Beck . |
| 4,016,650 | 4/1977 | Leusner et al. . |
| 4,368,040 | 1/1983 | Weissman ................................ 433/36 |
| 4,375,965 | 3/1983 | Weissman ................................ 433/37 |
| 4,432,728 | 2/1984 | Sharky ...................................... 433/37 |
| 4,543,062 | 9/1985 | Lee ............................................ 433/71 |
| 4,652,237 | 3/1987 | Cills .......................................... 433/37 |
| 4,693,683 | 9/1987 | Lee ............................................ 433/37 |
| 5,102,335 | 4/1992 | Getz .......................................... 433/38 |
| 5,297,960 | 3/1994 | Burns ........................................ 433/41 |
| 5,316,474 | 5/1994 | Robertson ................................ 433/38 |
| 5,336,086 | 8/1994 | Simmen et al. .......................... 433/37 |
| 5,370,533 | 12/1994 | Bushnell . |
| 5,478,235 | 12/1995 | Schuldt et al. ........................... 433/37 |
| 5,513,985 | 5/1996 | Robertson ................................ 433/38 |
| 5,520,539 | 5/1996 | Divjak . |
| 5,551,872 | 9/1996 | Mena . |
| 5,554,024 | 9/1996 | Ueda ........................................ 433/37 |
| 5,890,895 | 4/1999 | Tucker ...................................... 433/37 |

FOREIGN PATENT DOCUMENTS

| | | |
|---|---|---|
| 210868 | 11/1908 | Germany . |
| 1 079 276 | 4/1960 | Germany . |

*Primary Examiner*—Ralph A. Lewis
*Attorney, Agent, or Firm*—Vickers, Daniels & Young

[57] ABSTRACT

A dental impression tray having a handle and a mouthpiece is disclosed herein. The mouthpiece contains an upper portion and a lower portion defined as a means for laterally displacing excess impression material. The upper portion of the mouthpiece, which holds the impression material, is defined by outer and inner walls having arcuate shapes, a base attached to and extending the length of the bottom of the outer and inner walls, a plurality of elongated vent holes in the base, and a serpentine occlusal stop ridge extending from the top of the base. Therein the outer edge of the inner wall of the upper portion of the tray are a plurality of holes which force excess impression material to extrude to the means for laterally displacing excess impression material. Excess impression material extruded from the holes flow laterally across the horizontal surface and interlock with the excess material extruded from the elongated vent holes thereby securely attaching the impression material to the mouthpiece. Moreover, the elimination of the palate on the impression tray which creates the impression of the upper dentition by the present invention decreases the likelihood of inducing a patient's gag reflex. Extrusion of excess material to the horizontal surface also causes only the requisite amount of impression material to remain in the upper portion of the tray. The combination of the improvements of the present invention produces an overall more comfortable and accurate impression tray.

21 Claims, 4 Drawing Sheets

DENTAL IMPRESSION TRAY

This application is a continuation of Ser. No. 08,905,618, filed Jul. 25, 1997 is now U.S. Pat. No. 5,890,895.

FIELD OF THE INVENTION

The present invention relates generally to dental impression trays. More particularly, it relates to an improved impression tray which holds the impression material more securely and leaves only the requisite amount of impression material in the tray, thereby producing an improved impression for restoration.

BACKGROUND OF TEE INVENTION

Dental impression trays are widely known and used to produce impressions of sections of patient's dentition or the entire upper or lower portion of the dentition. The known process involves placing impression material into the impression tray and then inserting the tray into the patient's mouth to create the impression. The doctor maneuvers or manipulates the tray within the patients mouth relative to the teeth until the appropriate position is achieved and thereafter holds the tray in this position. The impression material cures while it is inside the mouth. Once completed, the doctor removes the cured impression from the patient's mouth after which it is used to create restorations.

Impression trays which are presently used typically are made of a combination of a mouthpiece and a handle. These devices are usually arcuate in shape to fit the contours of a patient's mouth. Moreover, the mouthpieces typically comprise an inner and outer wall and a base. The outer walls also have apertures which allow the impression material to escape during impressioning.

Recent trays even contain reservoirs in the base to allow the displaced impression material to be extruded during impressioning. These reservoirs are created by placing perpendicular slits underneath holes in the base of the tray. Thus, the reservoir is created by forming a cavity beneath the holes in the base of the tray. An example of a reservoir, as is typically used in presently known impression trays, is shown in U.S. Pat. No. 5,336,086. The purpose for these reservoirs is to allow displaced impression material to escape and to provide an interlock during impressioning. However, these devices generally fail to create a sufficient interlock to securely hold the impression material to the impression tray. That is, displaced material which is extruded as a rod through the holes in the base into the reservoirs, thus, when the displaced material cures or hardens, it generally retains the vertical rod like form. The absence of a means to properly position the displaced material beneath the holes in the base can result in the material hardening in a form which will not secure the material beneath the base in the reservoir. In which case, the intended interlock fails and subsequently the impression material does not hold securely to the impression tray.

As shown in FIG. 8, Presently used trays also contain straight ribs on the surface of the base which are intended to provide a more rigid tray. However, the alignment and positioning of these ribs can fail to adequately prevent patients' teeth from abutting the base of the tray. That is, presently used trays typically use straight ribs which are perpendicular to the inner and outer walls of the tray.

Furthermore, presently used trays also have holes in the inner wall of the tray. However, holes in the inner walls of presently used trays do not always adequately secure or attach excess impression material which has flowed thereto. Instead, as presently used, the holes in the inner walls of trays can sometimes serve merely to allow excess material to escape the tray and be extruded into the patients' mouth. That is, absent a means to assist the holes in the base in displacement of excess material which is extruded through them, the holes do not adequately secure hardened impression material which has flowed through. Thus, holes in the inner walls as presently used can not only fail to function as intended but can cause further discomfort to the patient.

The known prior art trays also contain a plate, extending across the palate of the patient, integral with or attached to the tray used to make impressions of the upper dentition. When the tray is inserted into the patient's mouth, the plate makes contact with the upper portion of the patient's mouth including the soft palate. Applying pressure to the soft palate in the upper portion of the patient's mouth with the plate of the prior art tray can induce a patient's gag reflex thereby causing severe discomfort for the patient. Furthermore, The possibility of inducing the patient's gag reflex limits the maneuverability of the tray by the doctor.

From the foregoing it will be understood that the currently used impression material does not adhere well to the plastic surface of the tray, largely due to the typical finish on the surface of the molded plastic article. Accordingly, a prior practice has been to coat the tray with bonding agent which adheres the impression material to the tray. Unfortunately, the bonding agent is toxic and extreme caution must be taken to avoid excess exposure to the patient. Therefore, the use of common bonding agents is expected to be banned.

Thus, an impression tray is needed which provides a solution to the aforementioned problems and thereby provides improvements in the formation of dental restorations.

SUMMARY OF THE INVENTION

An object of the present invention is to produce a dental impression tray having a means for laterally displacing excess impression material extruded beneath the upper portion of the tray which will enable the impression tray to produce an impression with the minimal amount of excess impression material, yet securely hold the impression material to the tray thereby creating a more accurate dental impression.

Yet another object of the present invention is to produce elongated vent holes so that sufficient amount of impression material extrudes into the means for laterally displacing excess impression material whereby material from said elongated holes interlock with displaced material from the inner wall forming an interlocking grid between the tray and the impression material.

It is also an object of the present invention to produce elongated vent holes so that only requisite amount of impression material remains in the base for proper impressioning of teeth.

Still another object of the present invention is to laterally displace excess impression material with a horizontal plate having an arcuate shaped flange attached peripherally thereto and extending the length of the base so that the plate forces displaced impression material thereon to be displaced laterally beneath the upper portion of the tray; and attached to said arcuate shaped flange, said horizontal plate for forcing displaced impression to flow laterally; and wherein the arcuate shaped flange and the horizontal plate define the means for laterally displacing excess impression material.

A further object of the present invention is to produce a means for laterally displacing excess impression material beneath the upper portion of the tray which comprises of a horizontal plate wherein the horizontal plate receives displaced impression material from the holes in the inner wall forcing it in the direction of displaced impression material received from the elongated holes in the base such that material received from the two types of holes interlock.

It is also an object of the present invention to produce an upper dentition impression tray which, unlike the palate of prior art impression trays, does not extend across the space within the upper portion of the mouth, the soft palate, thereby inducing a patient's gag reflex when tray is inserted therein.

It is another object of the present invention to utilize rods between the base and the displacement plate to form a lateral displacement chamber such that the rods provide proper spacing between the base and the horizontal plate and to increase the rigidity of the structure of the tray.

Other features, objects and advantages of the present invention will become apparent from a reading of the following description as well as a study of the appended drawings.

BRIEF DESCRIPTION OF THE DRAWINGS

A dental impression tray incorporating the features of the invention is depicted in the attached drawings which form a portion of the disclosure and wherein.

DESCRIPTION OF THE PREFERRED EMBODIMENTS

Figure 1:
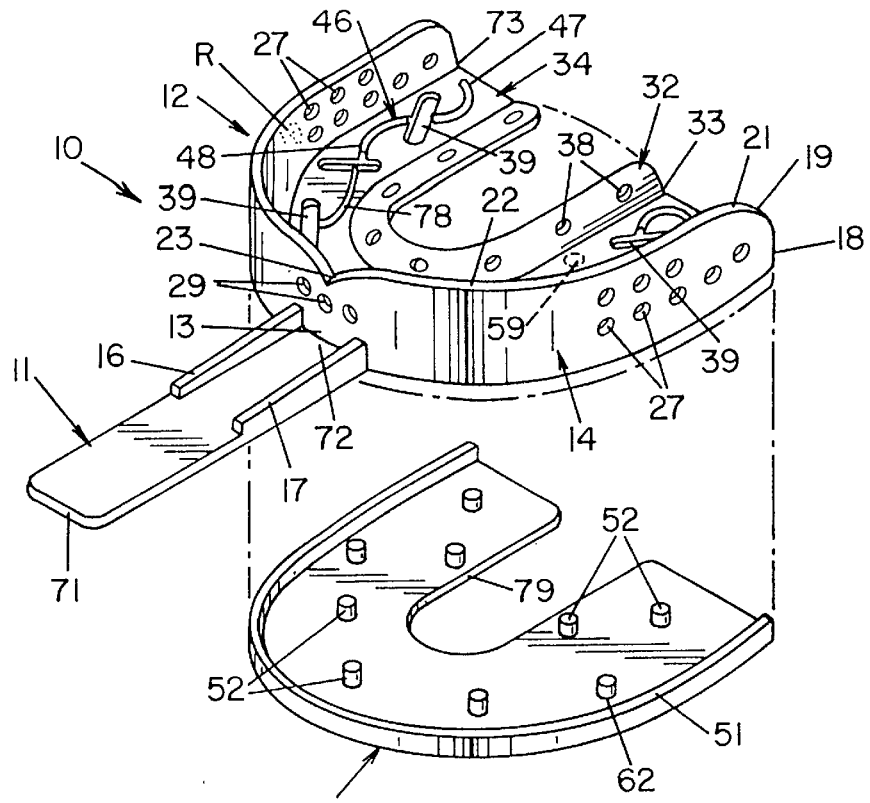
FIG. 1 is a perspective view of the dental impression tray showing the upper portion and the means for laterally displacing excess impression material beneath the upper portion.

Referring to the drawings for a better understanding of the function and structure of the invention, a preferred embodiment of the impression tray of the present invention is illustrated.

Figure 2:
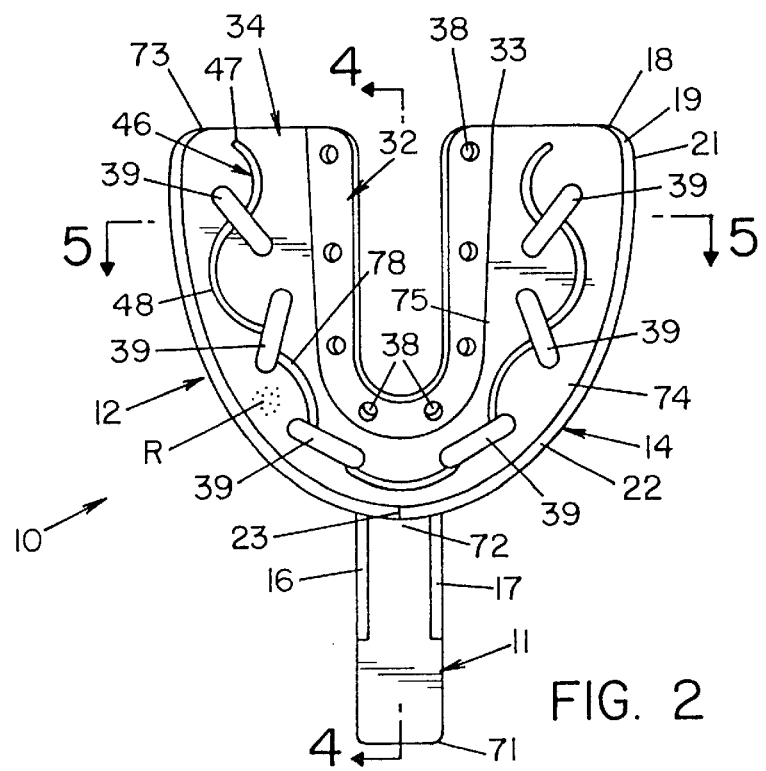
FIG. 2 is a top plan view of the present impression tray showing the elongated vent holes and the serpentine shaped occlusal stop ridges.
Figure 3:
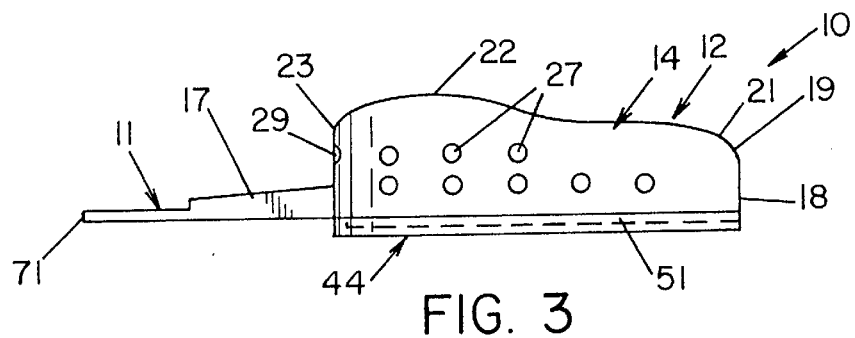
FIG. 3 is a side elevational view of the dental impression tray showing the upper portion and the means for laterally displacing excess impression material fixedly attached thereto.
Figure 4:
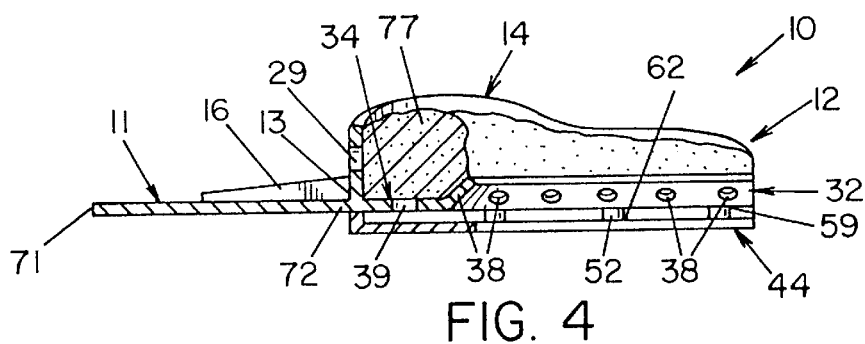
FIG. 4 is a sectional view taken along line 44 of FIG. 2 of the present impression tray showing the impression material before use.

The impression tray is indicated generally by the number 10 as shown in FIGS. 1–3. Preferably made of plastic, the present invention will be available in a number of different sizes to accommodate the size of the patient's dentition. The tray may have an integral handle 11 and an upper portion in the shape of a mouthpiece 12, or the handle 11 may be detachable from the mouthpiece 12. The handle 11 is preferably flat and has uniform thickness extending its entire length, with a curved first end 71. The entire length of the opposite end 72 of the handle 11 connects with the center bottom 13 portion of an outer wall 14 of the mouth piece 12. Atop handle 11 are a pair of gussets 16 and 17 serving to strengthen the connection of the of handle 11 to outer wall 14 of the mouthpiece 12.

Outer wall 14 of the upper portion of the tray is affixed to or integral with an outer edge of a generally C shaped base 34. Outer wall 14 begins at terminal point 18 and extends upwardly from base 34 forming an arcuate surface 19 until it reaches a point 21 where it forms an inclined surface having a moderate linear incline of approximately 15 degrees until it reaches a peak 22 whereupon it descends to a midpoint 23. Wall 14 then forms a mirror image from the midpoint 23 to a second terminal point 73. Passing through outer wall 14 are holes 27, preferably in pairs parallel to one another proximal terminal points 18 and 73. Holes 29 are also provided in spaced vertically relation to midpoint 23 of the outer wall 14.

An inner wall 32 of the upper portion extends upwardly from an inner edge of base 34 and is more "U-shaped" than outer wall 14. Walls 32, 14, and base 34 form a pocket 70 for the deposit of impression material 77. Inner wall 32 begins at a point 33 and extends the length of the inside of base 34 and flares upwardly at approximately a 45 degree angle relative to base 34. Evenly spaced apart on the inner wall 32 are holes 38.

As shown in FIG. 2, the base 34 is an arcuately shaped flat plate on the outside 74 and more "U-shaped" on the inside 75. It has a substantially continuous surface which is roughened or textured as indicated at R to avoid the traditional smooth surface of a plastic tray and has formed therein elongated vent holes 39.

Figure 5:
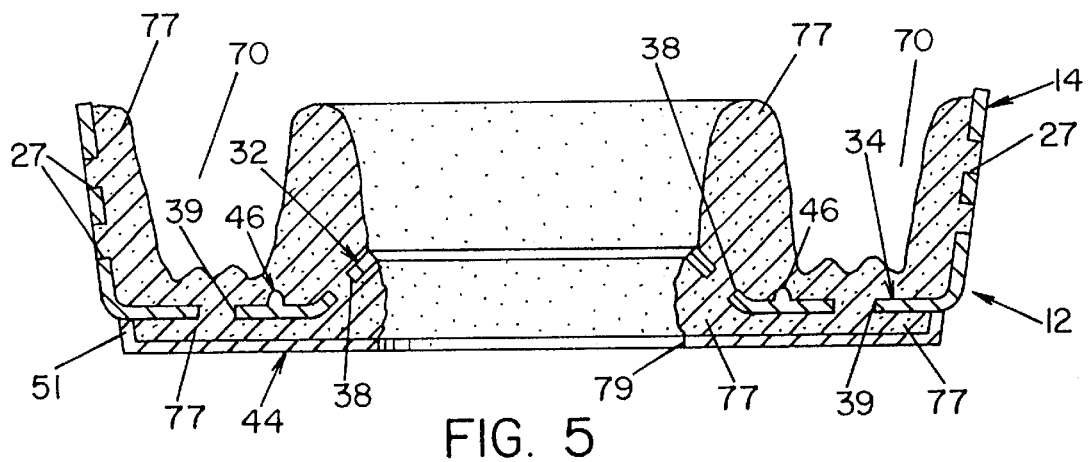
FIG. 5 is a sectional view taken along line 5-5 of FIG. 2 of the present invention showing displaced impression material received from holes in the inner wall interlocking with material which has flowed laterally from the elongated vent holes as well as material interlocked beneath the elongated vent holes.
Figure 6:
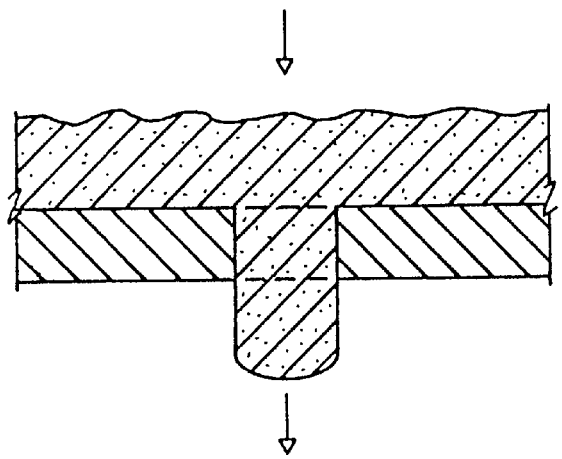
FIG. 6 is a sectional view of prior art showing how displaced material flows down into reservoirs.
Figure 7:
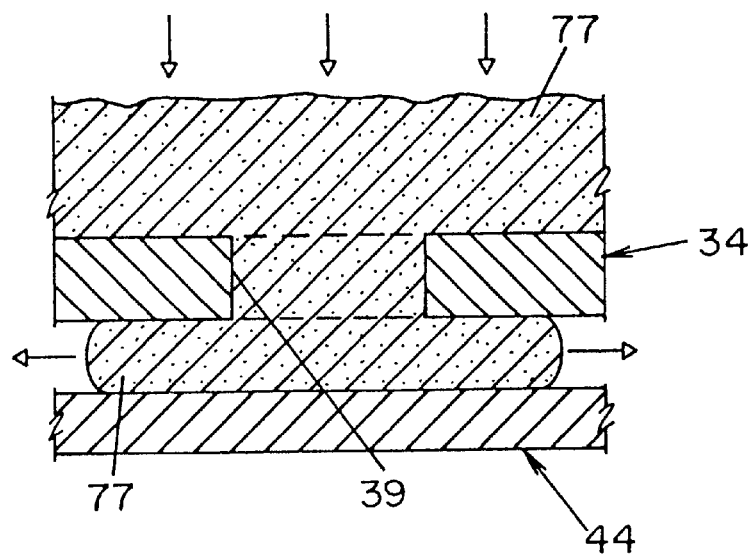
FIG. 7 is a sectional view showing displaced material protruding through the elongated vent holes to the horizontal plate.
Figure 8:
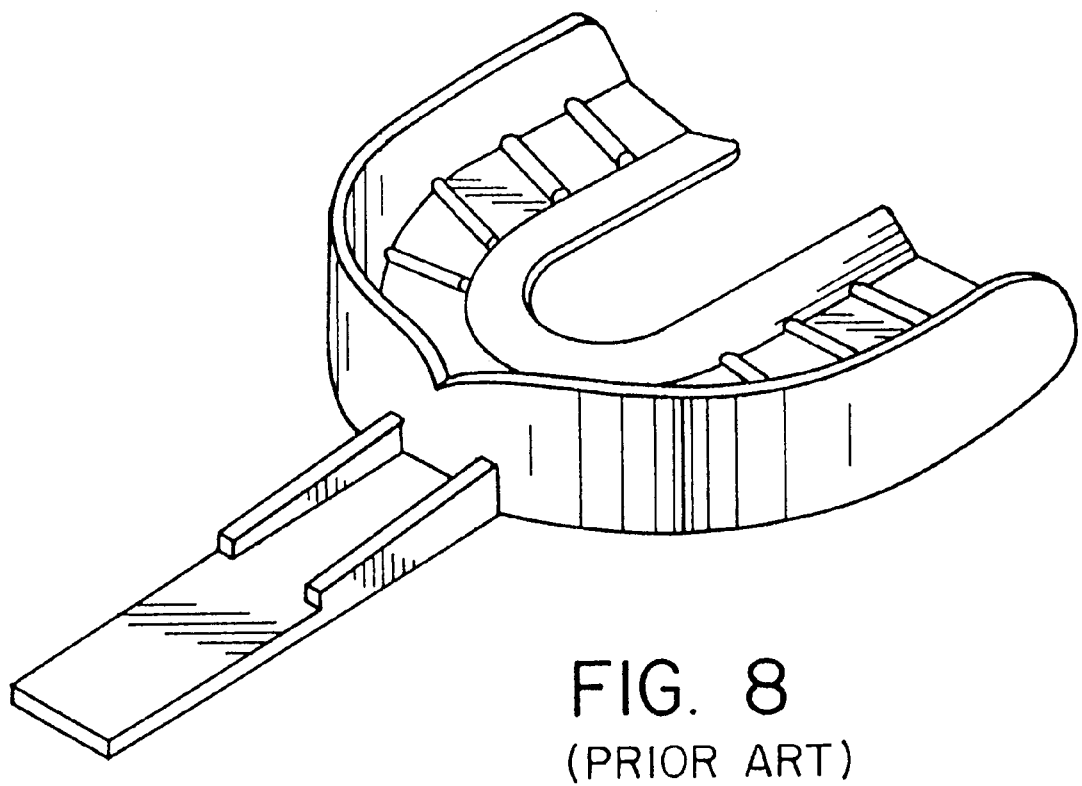
FIG. 8 is a perspective view showing the ribs of prior art impression trays.

As shown in FIG. 1, the means for laterally displacing excess impression material 77 beneath the base comprises an arcuately shaped horizontal plate 44 preferably having an arcuately shaped flange 51 and connected to mouthpiece 12 by a plurality of rods 52. Flowable impression material 77 as is traditionally used in the practice of forming an impression is deposited in mouthpiece between walls 14 and 32. As the dentist maneuvers the tray inside the patient's mouth, the patient's teeth displace excess impression material which extrudes through holes 27, 29, 38 and 39. Extruded material 77 abuts the flat surface of the horizontal plate 44 thus and is forced to flow laterally until it the extruding pressure is released. If sufficient flow is allowed the material extruded through various holes reach a point where it interlocks with material extruded through other. The elongated vent holes 39, shown in FIGS. 1 and 2, also allow enough impression material to be extruded down to the means for laterally displacing excess impression material 77 to insure lateral displacement of the material beneath base 34. Holes 38 also meter the extruded material such that only the requisite amount of material to form the desirable impression remains in the pocket 70 of the tray 15. The elongated vent holes 39 are formed on the base 34 diagonal to the inner and outer walls 32, 14, respectively. Also located on the base are serpentine shaped occlusal stop ridges 46 which prevent the patients' teeth from extending to base 34 of the tray and the elongated vent holes 39. The serpentine shaped occlusal stop ridges 39 begin at a point 47 and extend the entire length of the base 34. They are positioned such that the outer curves 48, 78 extend closely to either the outer wall 14 or inner wall 32 or whichever is closest to the particular curve. The arcuately shaped flange 51 is formed integrally with the peripheral edge of plate, 44 and extends toward the bottom of the base 34, thereby providing support for the upper portion of the mouthpiece and guiding laterally flowing displaced impression material back toward the excess material which is extruded through holes 38 in the inner wall 32. The arcuately shaped horizontal plate 44 impinges displaced impression material from the elongated vent holes 39 thereby causing the material to flow laterally. The lateral movement of the displaced impression material thereby interlocks the impression material to the tray by two means. First, as shown in FIG. 5, hardened impression material which has flowed laterally is dimensionally larger that the hole extruded through and thereby interlocks the material beneath the elongated vent holes 39. Whereas, as shown in FIG. 6, prior art reservoirs could create rods of the same dimension as the holes and which could be retracted into the holes. Additionally, the horizontal plate 44 also causes the displaced impression material received from the elongated vent holes 39 to flow laterally towards the excess impression material received from the holes 38 in the inner wall 32 thereby interlocking the connecting material and securing the hardened impression material to the tray 15. Rods 52, attached to the base 34 at a point 59 and to the horizontal plate 44 at a point 62, also serve to support the base 34 and provide rigidity to the tray's structure.

It is ostensibly noteworthy to mention that the inner wall 32, unlike the prior art, does not extend across the palate of the patient nor the soft palate, thereby avoiding contact with the surface of the soft palate of a patient's mouth when tray 15 is inserted therein. The absence of palate 36 in proximity with the soft palate of the patient's mouth reduces the likelihood of inducing a patient's gag reflex. This greatly decreases the discomfort to the patient and facilitates the maneuverability of the tray to the practitioner.

In operation the impression material is placed in the pocket 70 of the impression tray. Using the handle 11, the doctor then inserts the tray 15 inside the patient's mouth while carefully fitting the patient's teeth inside the pocket 70 of the tray as shown in FIG. 5. Once the tray is properly placed inside the patient's mouth, the doctor then maneuvers the tray until the appropriate position is achieved and thereafter holds the tray in this position so that the impression material can take the form of the patients' dentition. The distance created by the serpentine shaped occlusal stop ridges 46 prevents the patient's teeth from extending to the base 34 of the tray and the elongated vent holes 39. The excess impression material is extruded through the holes in the outer wall 14, the elongated vent holes 39, and the holes 38 in the inner wall 32. The excess impression material received through the elongated vent holes 39 then flows laterally across the horizontal plate 44. As shown in FIG. 5, Some of the material spreads laterally to the flange 51 attached to the horizontal plate 44 while the other laterally flows to the opposite end 79 of the base 34 where it connects with material received from the holes 27 in the inner wall. The hardened material then serves as an interlocking mechanism in both cases thereby firmly securing the impression material to the impression tray producing a more accurate impression of the patients' dentition for restoration.

There has been disclosed heretofore the best embodiment of the present invention contemplated. However, it will be obvious to those skilled in the art that there may be modifications to the present invention without departing from this present invention in its broader scope.

What is claimed is:

1. A dental impression tray for taking a patient's upper dentition comprising:

a generally flat U-shaped base having inner and outer U-shaped walls extending therefrom to define a volume into which a flowable impression material is placed for forming an impression;

said inner and outer walls having an upper margin with said inner wall's upper margin not extending across the palate of said patient and the space between confronting portions of said inner wall being free of obstructions; said inner wall extending a lesser distance from said base to said inner wall's upper margin than the distance said outer wall extends from said base to said outer wall's upper margin; said inner wall extending upwardly at an acute angle from said base and having a plurality of openings extending therethrough;

said base having a plurality of non-circular slots extending therethrough whereby said impression material flows through said slots and said openings to interlock about said base and inner wall to permit removal of said tray with hardened impression material, each of said slots adjacent to one another positioned in a non-parallel relationship to one another.

2. The impression tray as of claim 1 wherein said outer wall's upper margin having an anterior and posterior end, at least a portion of said outer wall's upper margin varying in distance from said base between said anterior and posterior ends.

3. The impression tray as of claim 1 wherein said outer wall includes a plurality of openings therethrough, the number of openings in said outer wall varying between the anterior and posterior portions of said outer wall.

4. The impression tray of claim 1 further including a plate spaced beneath said base and forming a pocket beneath said plate whereby impression material forced through said slots by the patient's teeth spreads into interlocking contact with impression material exiting said openings.

5. The impression tray as of claim 1 wherein said top surface of said base has a rough surface.

6. The impression tray as of claim 1 further including a plate spaced from said base and forming a pocket therewith for receiving displaced excess impression material extruded through said slots in said base when an impression of a patient's teeth is taken.

7. The impression tray as of claim 6 further including a plurality of rods positioned between said base and said plate to provide proper spacing between said base and said plate.

8. A dental impression tray for taking a patient's upper dentition comprising:

a generally flat U-shaped base having inner and outer U-shaped walls extending therefrom to define a volume into which a flowable impression material is placed for forming an impression;

said inner and outer walls having an upper margin with said inner wall's upper margin not extending across the palate of said patient and the space between confronting portions of said inner wall being free of obstructions; said inner wall extending a lesser distance from said base to said inner wall's upper margin than the distance said outer wall extends from said base to said outer wall's upper margin; said inner wall extending upwardly at an acute angle from said base and having a plurality of openings extending therethrough;

said base having a plurality of slots extending therethrough at an angular relationship to one another whereby said impression material flows through said slots and said openings to interlock about said base and inner wall to permit removal of said tray with hardened impression material, said base including a serpentine occlusal stop ridge extending upwardly from said base for preventing the patient's teeth from extruding all of said impression material from said base.

9. The impression tray of claim 8 wherein said acute angle is about 45°.

10. The impression tray of claim 9 further including a plate spaced beneath said base and forming a pocket beneath said plate whereby impression material forced through said slots by the patient's teeth spreads into interlocking contact with impression material exiting said openings.

11. The impression tray as of claim 10 further including a plurality of rods positioned between said base and said plate to provide proper spacing between said base and said plate.

12. The impression tray as of claim 8 wherein said outer wall's upper margin having an anterior and posterior end, at least a portion of said outer wall's upper margin varying in distance from said base between said anterior and posterior ends.

13. The impression tray as of claim 8 wherein said outer wall includes a plurality of openings therethrough, the number of openings in said outer wall varying between the anterior and posterior portions of said outer wall.

14. The impression tray as of claim 8 wherein said top surface of said base has a rough surface.

15. A dental impression tray for taking a patient's upper dentition comprising:

a generally flat U-shaped base having inner and outer U-shaped walls extending therefrom to define a volume into which a flowable impression material is placed for forming an impression;

said inner and outer walls having an upper margin with said inner wall's upper margin not extending across the palate of said patient and the space between confronting portions of said inner wall being free of obstructions; said inner wall extending a lesser distance from said base to said inner wall's upper margin than the distance said outer wall extends from said base to said outer wall's upper margin; said inner wall extending upwardly at an acute angle from said base and having at least one opening extending therethrough, said;

said base having at least one slot extending therethrough whereby said impression material flows through said slot and said opening to interlock about said base and inner wall to permit removal of said tray with hardened impression material, said outer wall having a plurality of openings therethrough, the number of openings in said outer wall varying between the anterior and posterior portions of said outer wall.

16. The impression tray as of claim 15 wherein said base includes a plurality of slots, each of said slots adjacent to one another positioned in a non-parallel relationship to one another.

17. The impression tray as of claim 15 including a serpentine occlusal stop ridge extending upwardly from said base for preventing the patient's teeth from extruding all of said impression material from said base.

18. The impression tray as of claim 15 wherein said outer wall's upper margin having an anterior and posterior end, at least a portion of said outer wall's upper margin varying in distance from said base between said anterior and posterior ends.

19. The impression tray of claim 15 further including a plate spaced beneath said base and forming a pocket beneath said plate whereby impression material forced through said slots by the patient's teeth spreads into interlocking contact with impression material exiting said openings.

20. The impression tray as of claim 19 further including a plurality of rods positioned between said base and said plate to provide proper spacing between said base and said plate.

21. The impression tray as of claim 15 wherein said top surface of said base has a rough surface.

* * * * *